Jan. 8, 1974 W. A. WARRINER Plant Pat. 3,431
ROSE PLANT
Filed Dec. 6, 1971
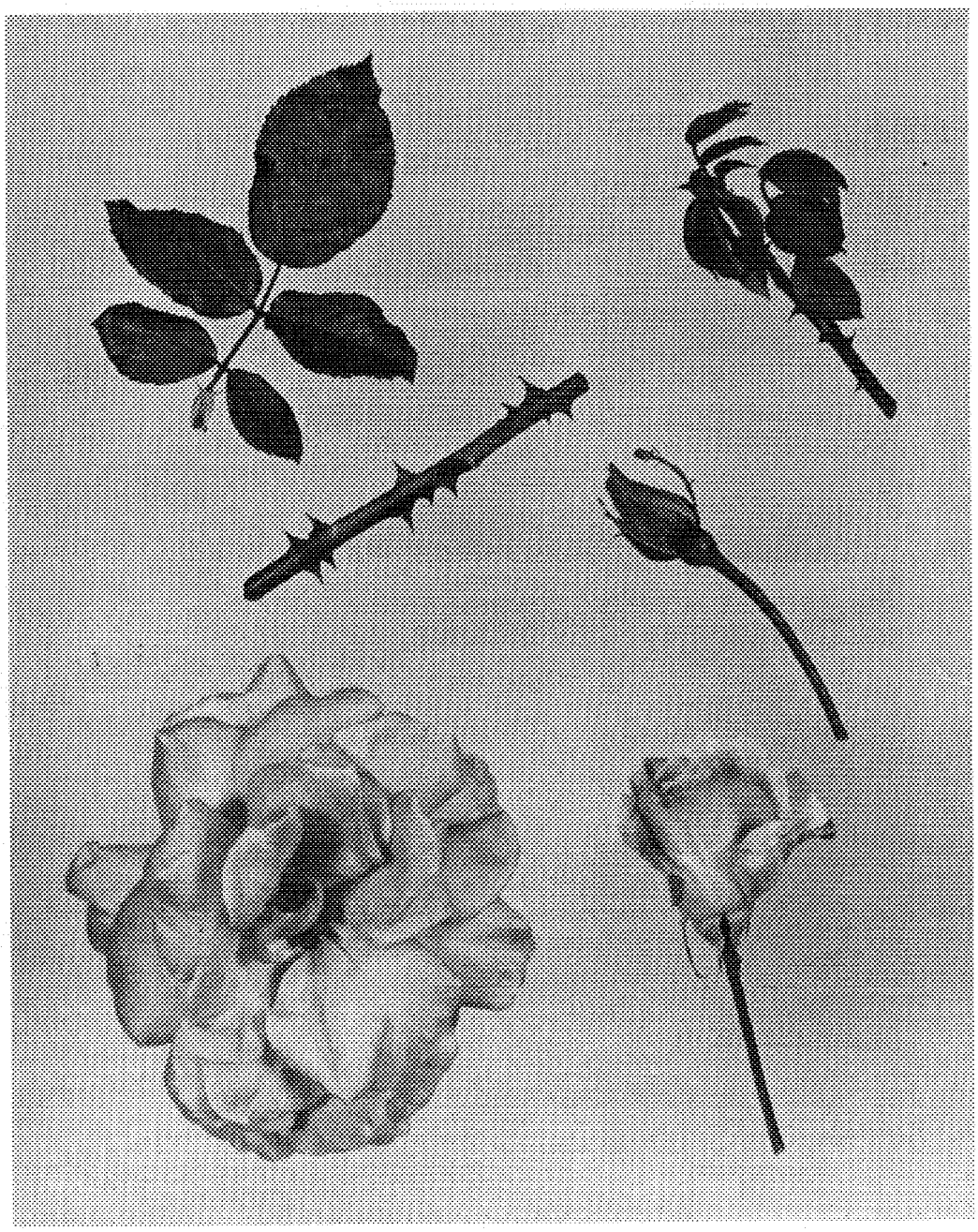
WILLIAM A WARRINER
INVENTOR
BUCKHORN, BLORE, KLARQUIST & SPARKMAN
ATTORNEYS United States Patent Office Plant Pat. 3,431
Patented Jan. 8, 1974

3,431
ROSE PLANT

William A. Warriner, Tustin, Calif., assignor to Jackson & Perkins Company, Medford, Oreg.

Filed Dec. 6, 1971, Ser. No. 205,421
Int. Cl. A01h 5/00
U.S. Cl. Plt.—11 1 Claim The present invention relates to a new and distinct variety of rose plant of the hybrid tea class originated by me by crossing the variety South Seas, U.S. Plant Pat. 2,184, by the variety Golden Masterpiece, U.S. Plant Pat. 1,284.

The primary objective of this breeding was to produce a new and improved variety of the hybrid tea class having a vigorous plant similar to the seed parent, South Seas, and with a color somewhere between the color of South Seas, coral-pink, and the color of Golden Masterpiece, yellow.

This objective was fully achieved along with other desirable improvements as evidenced by the following unique combination of characteristics which are outstanding in the new variety and which distinguish it from its parents as well as from all other varieties of which I am aware:

(1) A vigorous, upright, well branched, heavy caned habit of growth.
(2) Long pointed buds of Burnt Orange changing to Chinese Coral when partly opened.
(3) Large flowers whose petals do not curl back or quill and whose color slowly changes from Chinese Coral in the quarter open stage to a light carrot red.
(4) A light "fruit-like" fragrance.
(5) Large, leathery, deep green leaves.

Asexual reproduction of my new variety by budding as performed at Wasco, Calif., shows that the aforementioned characteristics come true to form and are established and transmitted through succeeding propagations.

The accompanying drawing shows typical specimens of the vegetative growth and flowers of my new variety in different stages of development, depicted in color as nearly true as it is reasonably possible to make the same in a color illustration of this type.

The following is a detailed description of my new rose variety, with color terminology in accordance with Wilson's "Horticultural Color Chart," except where ordinary dictionary meaning is indicated.

Parentage: Seedling
*Seed parent.*—South Seas, Pat. 2,184
*Pollen parent.*—Golden Masterpiece, Pat. 1,284
Classification:
*Botanic.*—Rosa hybrid
*Commercial.*—Hybrid tea

FLOWER (Observations were made in the afternoon at Irvine, Calif., in October.)

Blooming habit: Recurrent—continuous
Bud:
*Size.*—1½" when petals start to unfurl.
*Form.*—Pointed—long.
*Color.*—When sepals first divide—Burnt Orange (014/1). When half blown—inside of petals—near Chinese Coral (614), outer areas blending gradually to Indian Yellow (6/1) overcast with Chinese Coral (614). The yellow base is not sharply defined. Reverse of petals—Nasturtium Red (14/1) outer areas blending to Indian Yellow (6/1) overcast with Nasturtium Red (14/1) with streaks slightly darker. Base of petal on reverse side is near Lemon Yellow (4/1).

*Sepals.*—Color: Outer surface; nearest to Scheeles Green (860/3). Garnet Brown (00918) shading on most exposed side. There are a few gland tipped hairs on surface. Inner surface: near Scheeles Green (860/30) with normal amount of white tomentum. Three appendaged sepals lightly appendaged. Two unappendaged sepals have a few gland tipped hairs on edges.
*Receptacle.*—Color: Near Scheeles Green (860/2). Shape: Funnel. Size: Broad. Surface: Smooth.
*Peduncle.*—Length: Medium. Surface: Prickly. Color: Scheeles Green (860/3), except Garnet Brown (00918) on exposed side. Strength: Stiff, erect, heavy.
*Opening.*—Petals curl back slowly, but flatten out in open flower.
Bloom:
*Size.*—Large. Average size when fully expanded 4½"–5½".
*Borne.*—Singly, rarely several together.
*Stems.*—Long, strong.
*Form.*—When first open—cupped, with center covered by center petals. Permanence—flattens.
*Petalage.*—Number of petals under normal conditions, 40–50.
*Color.*—Center of flower: Upper side of petals—Carrot red (612/1). Reverse side of petals darker than upper side, close to Carrot red (612). Outer petals: Upper side of petals same. Reverse of petals when viewed from base to tip of petal, strong overlay of Indian yellow (6/1) is evident. General: tonality from a distance Carrot red (612) to (612/2).
*Discoloration.*—General tonality at end of first day—same as fresh. Third day—Center of flower Carrot red (612), most of outer petals Carrot red (612/2), outermost petals overlaid with a color near Spinel pink (0625/2).
*Fragrance.*—Slight.
Petals:
*Texture.*—Ordinary thickness.
*Surface.*—Inside—satiny. Reverse—satiny.
*Shape.*—Oval.
*Form.*—Flat.
*Arrangement.*—Loosely imbricated.
*Petaloids in center.*—Few.
*Persistence.*—Drop off cleanly.
*Lastingness.*—On the plant—long. As cut flower—fair.
Reproductive parts:
*Stamens, anthers.*—Small, many; regularly arranged around styles. Color—yellow.
*Stamens, filaments.*—Long. Color—yellow, reddish brown near base.
*Pollen.*—Color—gold yellow.
*Styles.*—Loosely separated, of uneven lengths; thin.
*Stigmas.*—Color—yellow.
*Ovaries.*—All enclosed in calyx.

PLANT

Form: Bush.
Growth: Vigorous, upright; branching.
Foliage: Compound of 5 leaflets.
*Size.*—Large.
*Quantity.*—Normal.
*Color.*—New foliage: Light green close to Scheeles Green (861/3) heavily overlaid with a color lighter than Oxblood Red (00823/3). Old foliage: Upper surface: Parsley Green (00962). Lower surface: Near Spinach Green (0960/3).
Leaflets:
*Shape.*—Oval.

*Texture.* — Upper side — leathery. Under side — smooth. Ribs and veins—prominent. Veins reddish on lower surface; midrib is reddishk above and below.

*Edge.*—Serrated.

*Serration.*—Single; small.

*Petiole.*—Rachis: Color—reddish upper side; light green lower side. Under side—prickles.

*Stipules.*—Long, glandular edges.

*Disease resistance.*—Resistant to mildew under normal growing conditions at Irvine, Calif.

Wood:

*New wood.*—Color—Light green; reddish on exposed side. Bark—smooth.

*Old wood.*—Color—green, sometimes streaky, reddish on exposed side. Bark—smooth.

Prickles:

*Quantity.*—On main stalks from base—ordinary. On laterals from stalk—ordinary.

*Form.*—Broad based; hooked downward.

*Color when young.*—Green and red.

*Position.*—Irregular.

*Small prickles.*—Quantity: On main stalks—few; on laterals—few. Color: Green.

I claim:

1. A new and distinct variety of rose plant of the hybrid tea class, substantially as herein shown and described, characterized particularly as to novelty by the unique combination of its vigorous, well branched plant, large dark green foliage, long pointed buds, burnt orange color opening to Chinese coral and fading lightly to a lighter carrot red.

No references cited.

ROBERT E. BAGWILL, Primary Examiner

PO-1050
(5/69)

UNITED STATES PATENT OFFICE
CERTIFICATE OF CORRECTION

Patent No. Plant No. 3431 Dated January 8, 1974

Inventor(s) WILLIAM A. WARRINER

It is certified that error appears in the above-identified patent and that said Letters Patent are hereby corrected as shown below:

Column 2, line 5, "(860/30)" should read --(860/3)--.
Column 3, line 14, "reddishk" should read --reddish--.

Signed and sealed this 2nd day of July 1974.

(SEAL)
Attest:

DWARD M.FLETCHER,JR.
ttesting Officer

C. MARSHALL DANN
Commissioner of Patents